(12) United States Patent
Usui

(10) Patent No.: US 7,048,031 B2
(45) Date of Patent: *May 23, 2006

(54) APPARATUS FOR CASTING DENTAL PROSTHESIS

(75) Inventor: Masaki Usui, Kyoto (JP)

(73) Assignee: Denken Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/465,870

(22) Filed: Jun. 20, 2003

(65) Prior Publication Data

US 2003/0234095 A1     Dec. 25, 2003

(30) Foreign Application Priority Data

Jun. 24, 2002   (JP) ............................. 2002-182390

(51) Int. Cl.
*B22D 41/00* (2006.01)
(52) U.S. Cl. ...................... 164/335; 164/322
(58) Field of Classification Search ............... 164/256, 164/258, 335, 338.1, 129, 130, 322–326
See application file for complete search history.

(56) References Cited

U.S. PATENT DOCUMENTS 6,386,265 B1 *  5/2002  Usui ........................ 164/114
6,488,074 B1 * 12/2002  Usui ........................ 164/256

FOREIGN PATENT DOCUMENTS

JP   2000-176629   6/2000
JP   2003-85426    3/2002

* cited by examiner

*Primary Examiner*—Kevin P. Kerns
(74) *Attorney, Agent, or Firm*—Oliff & Berridge PLC

(57) ABSTRACT

A new apparatus for casting dental prosthesis has been proposed, comprising a ring-placing section onto which plural rings are to be placed, a crucible holder for holding plural cylindrical crucibles, a burning unit with a furnace, a casting unit and a conveyer for conveying the ring or the crucible. The lifting state of the burning unit includes a base capable of rotating around a substantially horizontal axis, an orientation-maintaining mechanism for maintaining the base substantially horizontal and an orientation-changing mechanism for exerting an external force onto the base. The conveyer performs a position-correcting motion for correcting the position of the ring by lowering the gripper. The apparatus provides a management code to each crucible for preventing troubles or delay of work caused by the breaking of crucibles due to the aging.

6 Claims, 10 Drawing Sheets

BACK-AND-FORTH MOTION

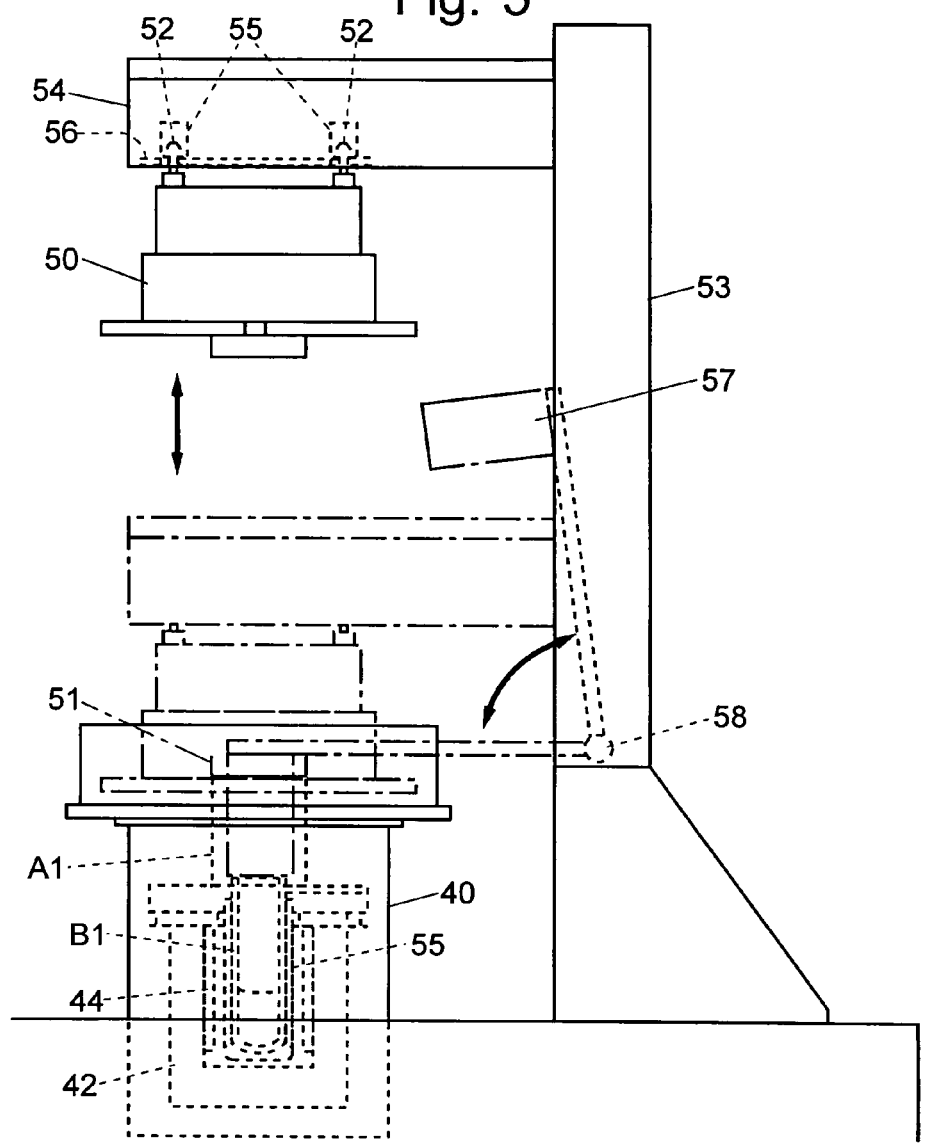
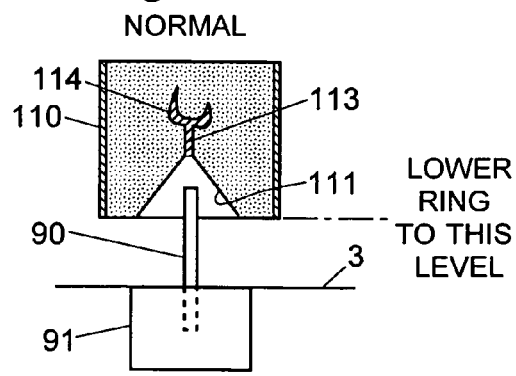
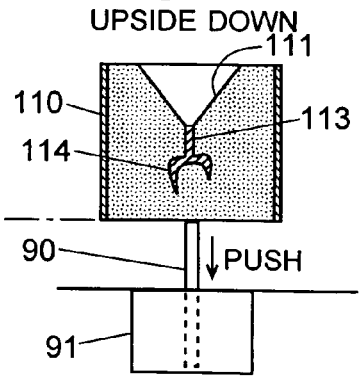

APPARATUS FOR CASTING DENTAL PROSTHESIS

The present invention relates to a casting apparatus for manufacturing dental prostheses, such as inlay, crown, base, implant, and upper parts of implants, from precious metals or non-precious metals.

BACKGROUND OF THE INVENTION

The lost wax process is a conventionally known method of manufacturing dental prostheses from precious metals or non-precious metals. FIG. 12 is a flowchart showing the process of dental casting according to the lost wax method.

First, a dentist or other individual takes a negative impression model of the mouth and teeth around the object part of a patient (Step S1). Using the negative impression, a dental technician manufactures a dental prosthesis as follows. First, a modeling material, such as gypsum, is poured into the negative impression, and solidifies the material to produce a positive model (Step S2). A desired type of casting model, such as an inlay or crown, for the positive model is created with a heat-subliming material, such as wax (Step S3). A sprue wire for forming a sprue runner is attached to an appropriate part of the casting model with wax (Step S4). After that, the casting model is detached from the positive model, and the free end of the sprue wire is pushed into a crucible former made of rubber (Step S5).

FIG. 13 is a front view of a casting model mounted on a commonly used crucible former. The crucible former 100 has a conical base 101 formed at its center, and a hole 102 for inserting a sprue wire 104 is formed on the top of the conical base 101. The hole 102 is filled with softened wax, and the free end of the sprue wire 104 (to which the casting model 103 is attached) is inserted in the soft wax. When the wax solidifies, the casting model 103 is fixed on the top of the conical base 101 with the sprue wire 104.

A metallic cylindrical ring (not shown) is fitted onto the crucible former 100 so that the casting model 103 is surrounded by the ring, and an investment material, such as gypsum or phosphate, is poured into the metallic ring to conceal the casting model 103 (Step S6). After the solidification of the investment material, the crucible former 100 is removed, the sprue wire 104 is pulled out, and the ring is heated to a high temperature. The heat burns off the wax inside, leaving a cavity corresponding to the sprue wire 104 and the casting model 103. Thus, a mold is obtained (Step S7).

Then, the mold is heated to a preset temperature, and molten metal is poured into a reservoir at the top of the mold, which is a reservoir having a shape corresponding to the conical base of the crucible former. The molten metal flows into the cavity through the sprue runner. This is so-called the "pouring" (Step S8). After the poured metal has cooled down and solidified, the mold is broken to take out the casting inside (Step S9). Then, unnecessary parts such as fringe metals along the sprue runner are removed from the casting, and after-treatments such as sanding the surface of the cast are carried out (Step S10). Thus, the prosthesis is completed.

Conventionally, in the work of Step S7, an electrical furnace, called a "ring furnace", is used to heat the ring to burn off the wax and to heat the mold to a preset temperature. The pouring work of Step S8 is carried out, for example, using a pressure casting apparatus with an inverting casting chamber (see the Japanese Unexamined Patent Publication No. 2000-176629, for example). In the aforementioned work, the operator should carry the crucible for melting the ring or ingot from one apparatus to another by himself or herself. Therefore, when various forms of prostheses are to be manufactured, it is necessary to spend a considerable amount of time and labor to carry out the casting work as described above. Further, the temperatures and time periods for burning the ring and for melting the metal must be appropriately determined depending on the selection of the investment material and alloy material, because a desired quality of prosthesis cannot be obtained when the settings are inappropriate. Conventionally, however, some pieces of prosthesis result in being defective (e.g. missing a part) as a result of inappropriate settings of the apparatuses, wrong order of work and/or accidental omission of work. This is inevitable when the casting work is manually carried out as described above.

In view of the above problem, the applicant has proposed an apparatus for casting dental prosthesis, disclosed in the Japanese Unexamined Patent Publication No. 2002-85426, which automatically performs the entire work relating to the casting. With this apparatus, the operator needs only to arrange a compound ring with a casting model embedded inside, and a crucible containing alloy ingots as casting material, at predetermined positions, and to set casting conditions as desired. After that, a completed casting is obtained in the ring in a preset period of time.

Though the above apparatus can automatically perform the burning and pouring, it cannot perform the basic work of setting rings and crucibles in the apparatus, which must be manually performed by the operator. Therefore, it is possible that the operator accidentally makes a mistake or omits a work process. Another problem, which is less serious than the aforementioned cases, is that the personal differences or other kinds of unevenness in the manner of working may cause a defect in the prosthesis, decrease the working efficiency or increase the manufacturing costs. Therefore, it has been demanded to provide the above apparatus with additional functionalities for decreasing human errors and other kinds of factors leading to defective products, or for correcting the errors, etc. Examples of the problems are as follows.

(1) The operator should correctly place the ring on a ring-placing platform. A displacement of the ring from the predetermined position often leads to the incorrect gripping of the ring by a gripping device (which is called the "gripper" hereinafter), which may make the ring fall down in the gripping process. To correct the placement of the ring, the apparatus disclosed in the Japanese Unexamined Patent Publication No. 2002-85426 is provided with movable pins used for pushing the ring into the correct position. This, however, requires a mechanism for moving the pins, which accordingly increases the production costs. It is desirable to construct a mechanism for correcting the position of the ring at a lower cost.

(2) As the crucible for melting the alloy ingots, a carbon-made crucible is used for the heating at relatively low temperatures, and a ceramic crucible is used for the heating at the temperature of 1400 C or higher. Ceramic crucibles gradually become brittle when they are repeatedly used. The possibility of cracking or breaking of the crucible rapidly increases when it is used more than approximately twenty times. If such a problem occurs in the course of the pouring process, it is necessary to not only stop the work but also perform other unnecessary work, such as the removal of the scattered casting material.

(3) Rings are burned as they are placed on a lifting stage. In the burning process, residues of burned wax or similar matters are deposited onto the lifting stage. If such residues are not removed, the ring placed on the lifting stage may be tilted by a piece of residue lying underneath, causing it to be on the verge of falling down or other hazardous situation. Accordingly, the operator must frequently take the trouble to clean the lifting stage to remove the residues. Neglecting this job may eventually lead to a discontinuation of the casting work.

(4) The operator may mistakenly set the ring upside down on the ring-placing platform. If this happens, the pouring cannot be correctly performed, which wastes not only time but also the casting material.

(5) For a casting material that has been used before, the appropriate temperature and time for melting the material is already known. For a material whose appropriate temperature and time for melting is unknown, it is often necessary to visually check the molten state of the alloy ingots in the crucible to determine at what temperature and in what time the material is adequately melted. Also, operators having little experience in the work may desire to visually check the molten state of the alloy ingots in the crucible to see whether or not the melting temperature and other parameters have been correctly set. To do such a visual check with conventional apparatuses, the operator is required to lean over the apparatus to look into the crucible, which is not only troublesome but also unsafe.

In view of the above problems, the present invention proposes an apparatus for casting dental prosthesis constructed to reduce the time and labor of the operator and compensate for mistakes and/or unevenness in the work to reduce defective products, improve the working efficiency and avoid the unnecessary increase in production costs.

SUMMARY OF THE INVENTION

To solve the above problem, an apparatus for casting dental prosthesis according to the first aspect of the present invention includes:

a) a ring-placing section, formed like a platform, onto which plural rings are to be placed, each ring having a casting model of a heat-subliming material embedded inside;

b) a crucible holder for holding plural cylindrical crucibles in a standing position, each crucible containing a casting material corresponding to each of the plural rings;

c) a burning unit having a vertically movable lifting stage onto which the ring is to be placed, and a furnace which covers the ring placed on the lifting stage when the lifting stage is elevated, and heats the ring to form a mold;

d) a casting unit having a chamber composed of a container for containing and heating the crucible, and a lid for covering the open top of the container while holding the mold in such a position where the sprue gate of the mold is located above the open top of the crucible contained in the container, and a chamber driver for melting the casting material in the crucible and then rotating the chamber from a normal position to a reversed position to pour the casting material into the mold; and e) a conveyer for conveying the ring or the crucible between the ring-placing section, the crucible holder, the burning unit and the casting unit, where the conveyer includes a gripper for holding the ring and the crucible, a vertical actuator for vertically moving the gripper, and a horizontal actuator for horizontally moving the gripper;

and the conveyer performs a position-correcting motion for correcting the position of the ring by lowering the gripper to a level close to the bottom of the ring and making a gripping motion with the gripper in advance of conveying the ring from the ring-placing section.

To use the apparatus according to the first aspect of the invention, the operator should prepare a cylindrical metal ring having a casting model of a heat-subliming material embedded inside, and set the ring on the ring-placing section. Also, the operator should put a casting material into the crucible and set the crucible in the crucible holder. Subsequently, the casting operation is started. In this operation, the conveyer controls the horizontal actuator to move the gripper into a position where it can grip the ring, and then controls the vertical actuator to lower the gripper to a level predetermined close to the bottom of the ring. For example, the gripper has plural fingers for gripping an object from the outside or, when the object to be gripped has a hollow body, from the inside. To grip the ring from the outside, the rods should be separately positioned around the ring, and then moved inwards until they contact the ring. To grip the ring from the inside, the rods should be first closely positioned, then inserted into the ring, and moved outwards.

Using the gripper, the present apparatus performs a position-correcting motion as follows. First, the gripper is lowered to a level close to the bottom of the ring. Then, the gripping operation as described above is performed with the gripper. In the gripping operation, the gripper pushes the ring from the outside or inside until the ring reaches the gripping point of the gripper, e.g. center of the rods. Thus, the ring can be brought to the correct position. It is not preferable to perform such a correcting operation with the gripper located at a level close to the upper end of the ring; when pushed in the upper part, the ring will fall down if it is greatly displaced from the correct position. Lowering of the gripper to a level close to the bottom of the ring effectively prevents such an occurrence. Thus, the present apparatus can assuredly correct the position of the ring on the ring-placing section.

After correcting the position of the ring, the conveyer ceases the gripping operation, moves the gripper up to a level where the gripper can hold the ring by the upper part, and performs the gripping operation again to securely hold the ring. After that, the conveyer conveys the ring onto the lifting stage of the burning unit. Thus, the ring is ready for the burning.

Thus, the apparatus according to the first aspect of the invention automatically corrects the position of the ring in advance of conveying the ring, so that the casting work can be performed without problem even when the operator has set a ring at a wrong position on the ring-placing section. The apparatus uses the conveyer for conveying a ring or crucible as a means for correcting the placement of the ring. This requires only a small amount of additional cost for implementing the function for correcting the position of the ring.

To solve the above problem, an apparatus for casting dental prosthesis according to the second aspect of the present invention includes a crucible holder for holding a cylindrical crucible in a standing position with a casting material contained inside, a casting unit having a container for containing and heating the crucible, and a conveyer for conveying the crucible from the crucible holder to the container, wherein the crucible has a management code indicated on its upper part, and the apparatus further includes:

a) a crucible rotator for holding the crucible in a standing position and rotating the crucible at a preset speed around a vertical axis passing through the center of the crucible;

b) a code reader for reading the management code on the crucible while the crucible is rotated by the rotator;

c) a usage history manager for managing the usage history of each crucible based on the management code read by the code reader; and d) a controller for checking whether the cumulative usage count of the crucible has attained a predetermined count, and for determining, based on the result of the checking, whether the casting operation using the crucible is acceptable.

In the apparatus according to the second aspect of the invention, the crucible held by the crucible holder is set in the crucible rotator by, for example, the conveyer, and then rotated at a preset speed. Then, the code reader discerns the management code indicated on the upper part of the crucible rotated. An example of the code reader is an optical reader, which extracts information from the ON/OFF pattern of the reflection or the changing pattern of reflectivity. The usage history manager manages the usage history for every management code, that is, for every crucible, providing information about how many times each crucible has been used. The controller obtains information about how many times the crucible that is about to be activated has been used, and determines whether its usage count has reached a limit count. The limit count is predetermined with reference to a critical count where the probability of breaking or cracking of the crucible rapidly rises. The critical count can be estimated for each type of the crucible based on experimental and empirical data about the durability and other properties. If the usage count has reached the limit count, the controller disallows the casting operation to be performed with that crucible, because further use of that crucible would be dangerous. Thus, for example, the controller controls the conveyer to return the crucible to the crucible holder and take out another crucible to perform the casting operation.

In the above case, it is preferable to alarm the operator, by means of a display or sound, when the crucible is no longer usable. Recognizing the alarm, the operator may dispose the crucible.

Thus, the apparatus according to the second aspect of the invention automatically disallows the use of the crucible if its usage count has reached a predetermined number where the cracking, breaking or other problem is highly probable, and gives a precaution to the operator. The process of melting the casting material and pouring the casting material into the mold is always performed with a crucible having adequate durability. This ensures a high degree of safety even in the case of using a ceramic crucible or similar crucible that becomes brittle when it is repeatedly used. Furthermore, the present apparatus improves the working efficiency because unnecessary work for restoration from the trouble decreases. In addition, the present apparatus reduces the workload of the operator because it is no longer necessary to manually manage the usage history of every crucible.

To solve the above problem, an apparatus for casting dental prosthesis according to the third aspect of the present invention includes:

a) a ring-placing section onto which a ring is to be placed with a casting model of a heat-subliming material embedded inside;

b) a burning unit having a vertically movable lifting stage onto which the ring is to be placed, and a furnace which covers the ring placed on the lifting stage when the lifting stage is elevated, and heats the ring to form a mold;

c) a casting unit having a chamber composed of a container for containing and heating the crucible with a casting material contained inside and a lid for covering the open top of the container while holding the mold in such a position where the sprue gate of the mold is located above the open top of the crucible contained in the container, and a chamber driver for melting a casting material in the crucible and then rotating the chamber from a normal position to a reversed position to pour the casting material into the mold; and d) a conveyer for conveying the ring between the ring-placing section, the burning unit and the casting unit, and the lifting stage of the burning unit includes:

a base capable of rotating around a substantially horizontal axis, an orientation-maintaining mechanism for maintaining the base substantially horizontal when no external force is exerted on the base, and an orientation-changing mechanism for exerting an external force onto the base to change the orientation of the base when the base is lowered to a predetermined level.

The apparatus according to the third aspect of the present invention is constructed to heat the ring in the furnace with the base elevated. After the heating, the base is lowered to a certain level, where the conveyer takes the ring away from the base. Then, only the residues of the burned wax and other matters produced in the burning process remain on the base. Next, the base is further lowered to a predetermined position, where a part of the base receives an external force from the orientation-changing mechanism. This releases the base from the state of being maintained substantially horizontal by the orientation-maintaining mechanism, so that the base tilts. The inclination of the base makes the residues slide down and be discarded, and the ring to be used next is placed on the base thus cleaned. Therefore, the ring will never be tilted or made to fall down by a piece of residue lying underneath.

Thus, the apparatus according to the third aspect of the invention makes it unnecessary to manually clean the base every time the burning of the ring is completed, so that the workload of the operator is reduced. Furthermore, there is no possibility that the burning work is discontinued by a falling down of the ring, which often happened when the operator forgot to clean the base. Thus, the prosthesis can be efficiently manufactured.

To solve the above problem, an apparatus for casting dental prosthesis according to the fourth aspect of the present invention includes:

a) a ring-placing section onto which a ring is to be placed with a casting model of a heat-subliming material embedded inside, where the ring has a reservoir on one side;

b) a burning unit having a vertically movable lifting stage onto which the ring is to be placed, and a furnace which covers the ring placed on the lifting stage when the lifting stage is elevated, and heats the ring to form a mold;

c) a casting unit having a chamber composed of a container for containing and heating the crucible with a casting material contained inside and a lid for covering the open top of the container while holding the mold in such a position where the sprue gate of the mold is located above the open top of the crucible contained in the container, and a chamber driver for melting a casting material in the crucible and then rotating the chamber from a normal position to a reversed position to pour the casting material into the mold;

d) a conveyer for conveying the ring or the crucible between the ring-placing section, the crucible holder, the burning unit and the casting unit, where the conveyer includes a gripper for holding the ring and the crucible, a vertical actuator for vertically moving the gripper, and a horizontal actuator for horizontally moving the gripper; and e) a ring reversion detector having a movable element to be pressed by the opposite side of the ring onto which the reservoir is not present when the ring gripped by the conveyer is lowered to a preset level, and a detector for detecting the motion of the movable element.

The apparatus according to the fourth aspect of the present invention detects the reversion of the ring as follows. First, the operator places a ring on the ring-placing section. Then, the conveyer grips the ring, conveys it to the ring reversion detector, and lowers it to a predetermined level. This level is determined so that the ring does not press the movable element down when the reservoir is on the lower side, whereas the ring presses the movable element down when the reservoir is on the upper side, meaning that the ring is upside down. This allows the detector to detect the upside-down placement of the ring before the burning process. When the ring is placed upside down, the apparatus can take a proper action, such as stopping the operation before the burning of the ring is started.

Thus, the apparatus according to the fourth aspect of the invention improves the efficiency of the manufacturing process by eliminating the possibility of continuous and fruitless work resulting from the upside-down placement of the ring. The apparatus also prevents unnecessary consumption of the casting material ready for use at the moment by halting the heating and melting process of the casting material.

To solve the above problem, an apparatus for casting dental prosthesis according to the fifth aspect of the present invention includes:

a) a casting unit having a chamber composed of a container for containing a cylindrical crucible with a casting material contained inside and a lid for covering the open top of the container while holding a mold in such a position where the sprue gate of the mold is located above the open top of the crucible contained in the container, a crucible heater for heating the crucible contained in the container to melt the casting material in the crucible, and a chamber driver for rotating the chamber from a normal position to a reversed position to pour the casting material into the mold after the casting material is melted in the crucible;

b) a conveyer for conveying the crucible into the container before the heating and pouring of the casting material, and for conveying the mold to a position above the crucible contained in the container;

c) a casing for containing the casting unit and the conveying unit;

d) an inclination determiner for maintaining a rotational position of the chamber so that the crucible is inclined by a preset angle before the mold is conveyed to the position above the crucible contained in the container; and e) a crucible inspection mechanism having at least one mirror located so that the inside of the crucible inclined can be observed through it, a lens for enlarging the image reflected in the mirror, a lighting device for illuminating the inside of the crucible inclined, and an opening formed in the outside of the casing for allowing a view of the enlarged image created by the lens.

In the apparatus according to the fifth aspect of the invention, the inclination determiner rotates the chamber by a preset angle in response to, for example, a predetermined commanding operation by the operator. Then, the chamber is halted at that position, with the crucible inclined. When the crucible is thus inclined, the mirror projects an image of the inside of the crucible to the lens, which in turn enlarges the image. The enlarged image can be viewed from the outside through the opening. Thus, the operator can observe the inside of the crucible, and visually check whether the casting material contained in the crucible has been melted and is glowing. For a casting material that does not glow when heated, the molten state of the material can be easily checked by illuminating the inside of the crucible with the lighting device and checking whether the surface of the material is like a mirror.

Thus, the apparatus according to the fifth aspect of the invention allows the operator to check the molten state of the casting material in the crucible from the outside of the casing, if necessary. Therefore, even when a casting material whose melting conditions are unknown or uncertain is used, it is possible to perform the pouring process after ascertaining that the casting material is adequately melted. The molten state can be checked from the outside of the casing, which provides a high degree of safety.

BRIEF DESCRIPTION OF THE DRAWINGS

FIG. 5 is a right side view of the casting unit F of the automatic casting apparatus of the embodiment.

FIGS. 6A and 6B are outlined drawings of the ring reversion detector H of the automatic casting apparatus of the embodiment.

DETAILED DESCRIPTION OF A PREFERRED EMBODIMENT

An automatic casting apparatus as an embodiment of the present invention is described below, referring to the attached drawings.

Figure 1:
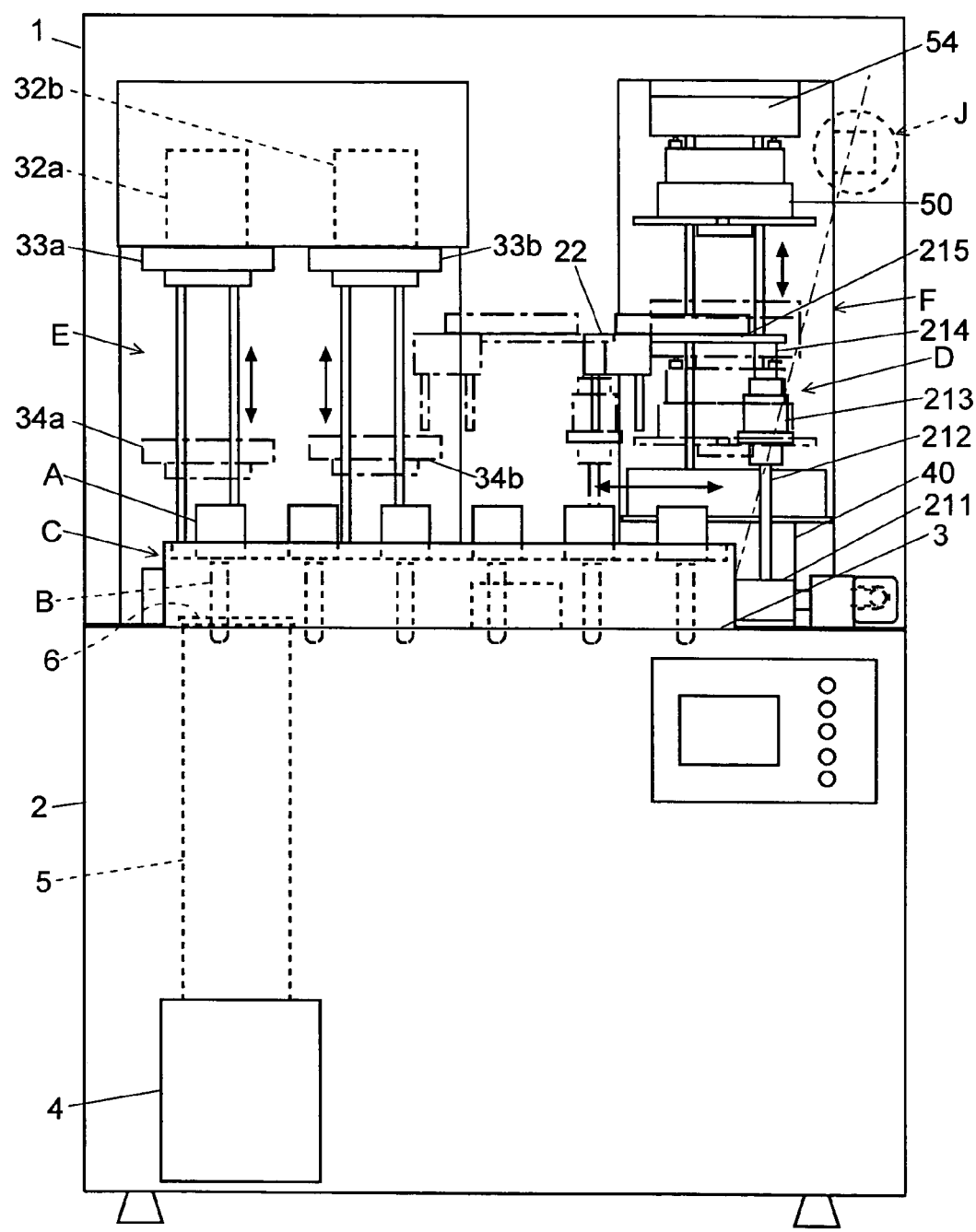
FIG. 1 is a front view of the main part of an automatic casting apparatus as an embodiment of the present invention.
Figure 2:
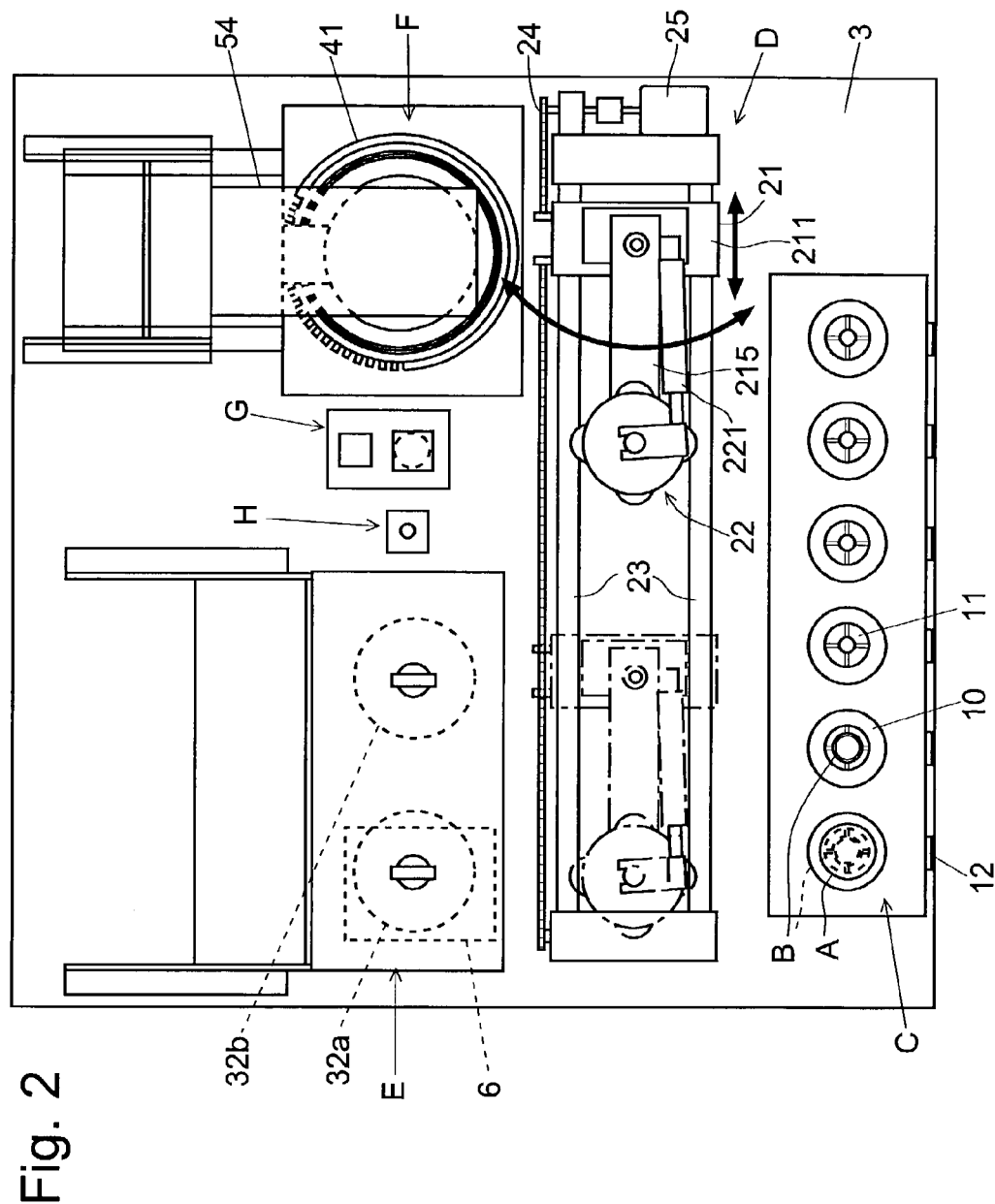
FIG. 2 is a top view of the main part of the automatic casting apparatus of the embodiment.

As shown in FIGS. 1 and 2, the casting apparatus has a long rectangular body, the lower part of which is a box 2 containing a control circuit for controlling the mechanical and electrical operations, and mechanisms for supplying compressed air. The top of the box 2 serves as a table 3 on which several devices are mounted for various kinds of work, which will be described later. The top of the table 3 is covered with a cover 1 having a transparent door (not shown) at its front side. The cover 1 ensures the safety of the operator, and prevents litters, dusts and other foreign matters from falling onto the table 3.

On the table 3, a ring/crucible-placing platform C, having the capacity of six rings A and six crucibles B, is provided at the front, and a conveyer D for holding and conveying the ring A or crucible B is provided behind the ring/crucible-placing platform C. Behind the conveyer D, a burning unit E is provided on the left side, and a casting unit F on the right side. The burning unit E is capable of simultaneously heating two rings A under independently controlled temperatures. The casting unit F is used for heating a crucible B to melt the alloy ingots contained in the crucible B, and for pouring the molten metal into the ring A, which has a mold formed by the burning process. The ring/crucible-placing platform C, conveyer D, burning unit E and casting unit F are the main components of the apparatus. In addition, the apparatus includes a crucible usage history manager G for managing the usage count of each crucible B, and a ring reversion detector H for detecting the reversion of the ring, both located between the burning unit E and the casting unit F. In addition, a crucible inspection mechanism J is provided above the table 3, which offers a view of the inside of the crucible B set in the casting unit F.

The table 3 has a ring collection port 6 for collecting the ring after the completion of the pouring process. The ring collection port 6 has a door that is pushed open by the ring when a ring is placed on it. Then, the ring falls from the ring collection port 6 through the falling passage 5, and is received by a collection chamber 4 located at the bottom. The collection chamber 4 can be taken out from the front side of the box 2.

In the following description, the ring A is referred to by different numerals depending on its state. The first state of the ring, obtained by removing the crucible former after the solidification of the investment material, is referred to by numeral A1. The second state of the ring, obtained by heating the ring to burn off the wax, is referred to by numeral A2. Also, the crucible B is referred to by different numerals depending on the state of the alloy contained inside. Numeral B1 is used to denote the crucible containing solid alloy ingots, and numeral B2 is used to denote the crucible containing molten alloy.

The detailed structure and operation of each of the components is as follows.

(1) Ring/crucible-placing Platform C (FIGS. 1 and 2)

The ring/crucible-placing platform C has cavities 11 for holding six crucibles B in the standing position aligned laterally with preset intervals. The cavity 11 is designed so that the upper end of the crucible set therein is lower than the circumferential plane. This plane corresponds to the bottom of a ring-placing area 10 onto which the ring A is to be placed. Thus, each crucible set in the cavity 11 is paired with a ring A into which the casting material contained in the crucible is to be poured. The ring/crucible-placing platform C has six indicators 12 corresponding to the six pairs of the ring and crucible on the front side. The indicator 12 is lit when the crucible or ring corresponding to the indicator 12 is being conveyed at that moment.

Figure 3A:
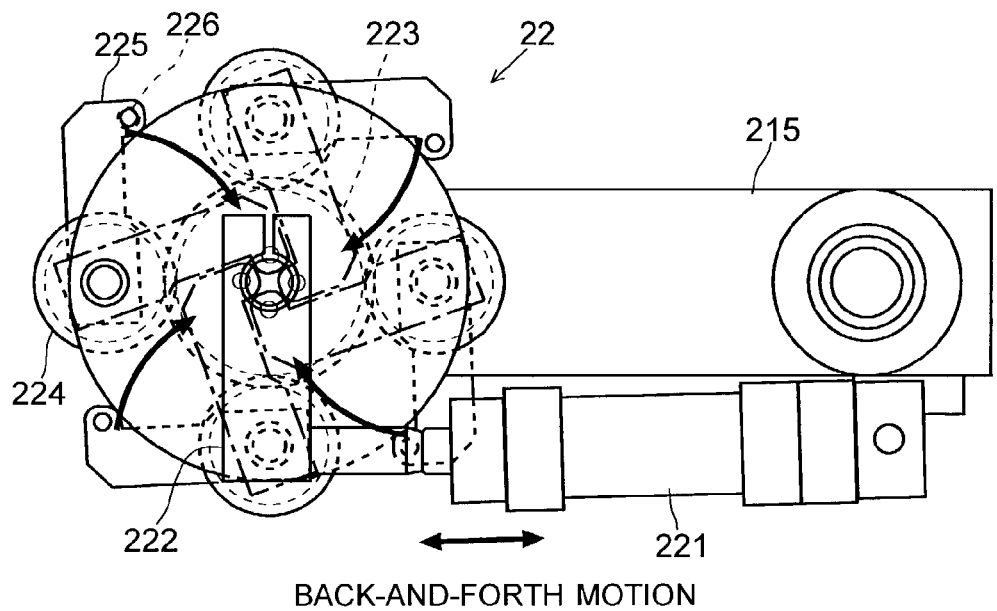
FIG. 3A is a top view of the conveyer D of the automatic casting apparatus of the embodiment.
Figure 3B:
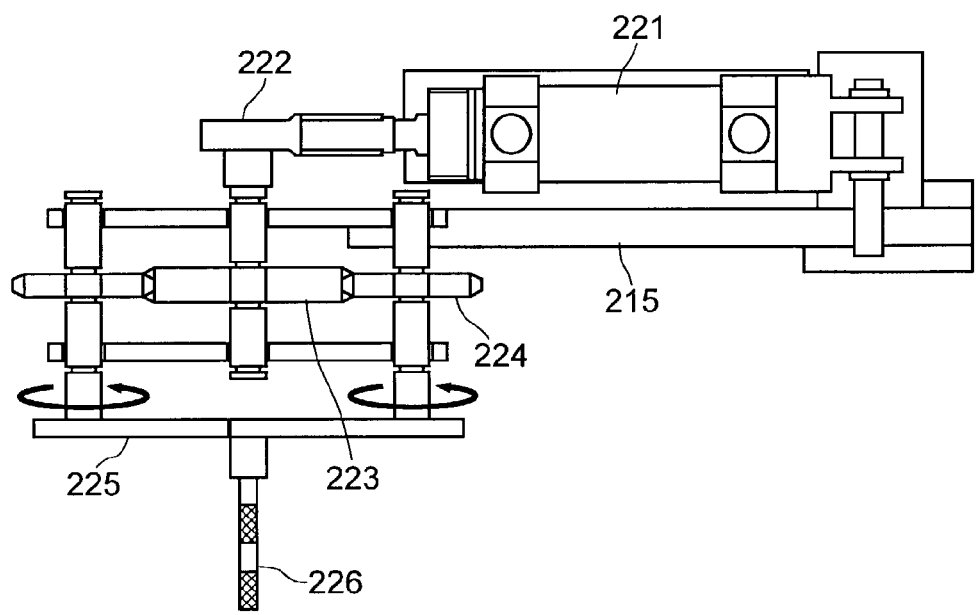
FIG. 3B is a side view of the conveyer D.

(2) Conveyer D (FIGS. 1, 2 and 3)

The conveyer D includes a carriage 21 with a gripper 22 for gripping the ring A or crucible B mounted on its top. The carriage 21 includes: a base 211 which can slide along a pair of guide rails 23 supported in parallel that penetrate through the base 211; an expansion leg 212 vertically penetrating the base 211; a bearing base 213 fixed at the upper end of the leg 212; a main shaft 214 vertically held by the bearing base 213; and an arm 215 extending horizontally, one end of which is fixed to the upper end of the main shaft 214. The gripper 22 is mounted on the other end of the arm 215. The base 211 is fastened to a chain belt 24 driven by a motor 25. According to the rotation of the motor 25, the base 211 moves back and forth along the guide rails 23.

The gripper 22 includes: an air cylinder 221, one end of which is fixed to the arm 215; a connector 222 connected to the other end of the cylinder 221; a main gear 223 that rotates around a vertical shaft held by the arm 215 when actuated by the air cylinder 221 via the connector 222; four pieces of sub gears 224 engaged with the main gear 223, each rotating around a vertical shaft; and four pieces of movable elements 225 each having a finger fixed to its lower side. When the main gear 223 rotates, the four sub gears synchronously rotate. According to the direction of the rotation, the four fingers 226 move closer to or away from each other. In this specification, the two types of motions of the fingers 226 for holding the crucible A or ring B are generally called the "gripping", regardless of the moving direction of the fingers 226.

The conveyer D can perform the following motions: grip the crucible A or ring B with the four fingers 226 driven by the air cylinder 211, raise or lower the fingers 226 (and the gripper 22) by expanding or contracting the leg 212; and move the fingers 226 in a horizontal plane by sliding the base 211 along the guide rails 23 and swinging the arm 215 around the main shaft 214. Furthermore, the conveyer D performs the position-correcting motion for correcting the position of the ring A on the ring/crucible-placing platform C in advance of gripping the ring A, as will be described later.

The sliding motion of the carriage 21 is produced by the driving force of the motor 25. The raising/lowering motion of the arm 215 with the expansion/contraction of the leg 212, the swinging motion of the arm 215 with the rotation of the main shaft 214, and the gripping/releasing motion of the fingers 226 are produced by an air motor or air cylinder using air pressure. It should be noted that the present invention allows the use of the electric driving force or other driving force.

Figure 4:
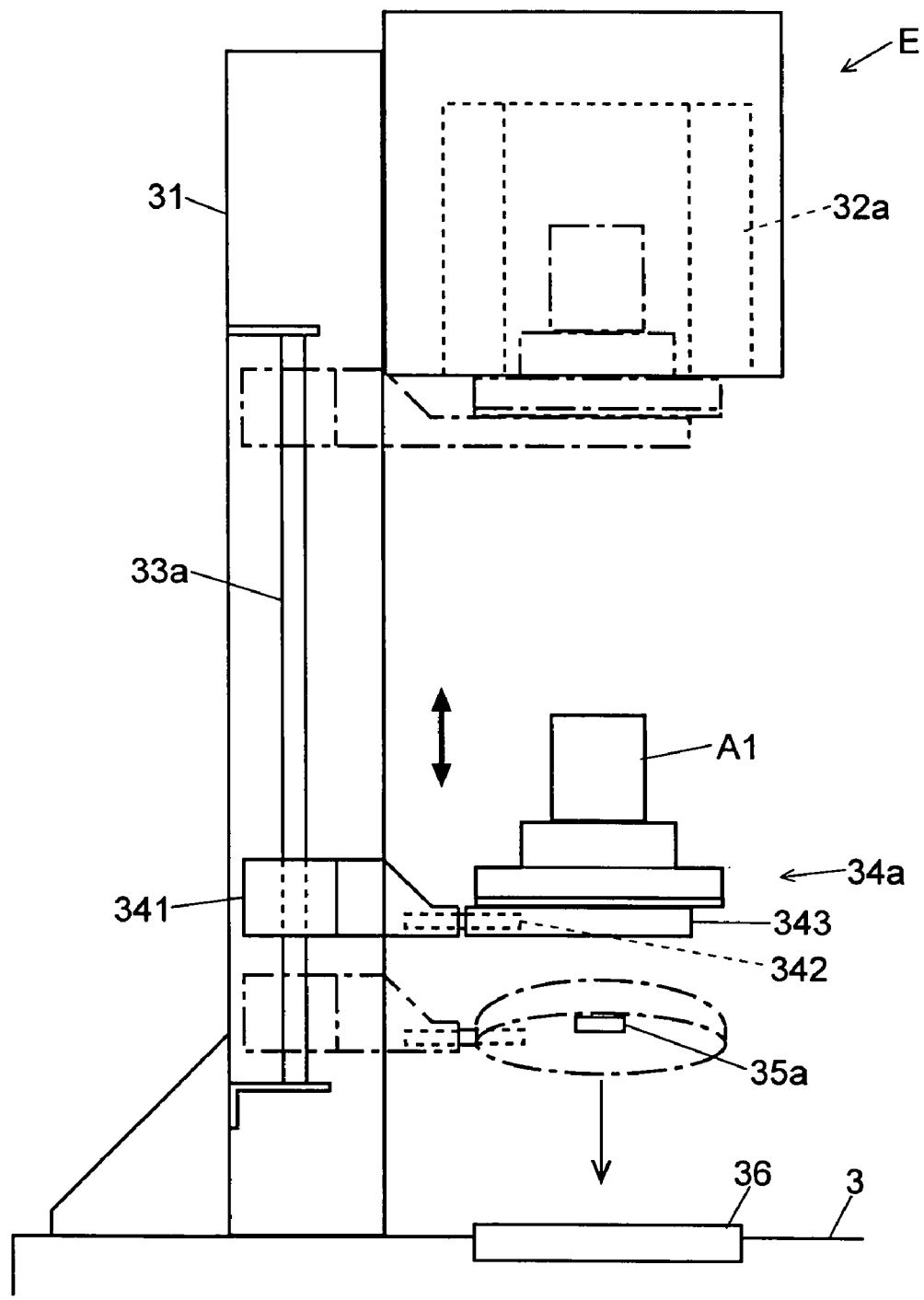
FIG. 4 is a left side view of the burning unit E of the automatic casting apparatus of the embodiment.

(3) Burning Unit E (FIGS. 1, 2 and 4)

In the burning unit E, a pair of furnaces 32a and 32b, aligned side by side in the direction of the guide rails 23, are mounted on the upper part of a stand 31. Under the furnaces 32a and 32b, two lifting stages 34a and 34b, which can independently slide along vertical guide rails 33a and 33b, respectively, are provided. The lifting stage 34a includes an elevator 341 through which the guide rail 33a penetrates, a horizontal shaft 342 extending in the back-to-front direction, and a rotator 343 which can rotate clockwise and counter-clockwise around the horizontal shaft 342. The rotator 343 is maintained horizontal by the action of a spring (not shown) when no other force is externally applied to it. The other lifting stage 34b is constructed similar to the lifting stage 34a.

On one side of the stand 31, three switches (not shown) are provided at three different levels to detect the lifting stage 34a or 34b when it is at one of the three levels. The highest switch detects the lifting stage 34a or 34b when the stage has reached the highest position. In this position, the lifting stage 34a or 34b closes the bottom opening of the furnace 34a or 34b, forming a tightly closed space within the furnace with the ring A contained inside on the lifting stage 34a or 34b.

The intermediate switch detects the lifting stage 34a or 34b at the position where the conveyer D can place the ring A onto or take the ring A from the lifting stage 34a or 34b with the gripper 22. This position is called the "intermediate position" hereinafter. The lowest switch detects the lifting stage 34a or 34b when the stage has reached the lowest position. Slightly above the lowest position, a pair of projections 35a and 35b are provided, each of which located so that it interferes with an end of the rotator 343 of the lifting stage 34a or 34b. In the course of lowering from the intermediate position to the lowest position, the rotator 343 of the lifting stage 34a or 34b collides with the projection 35a or 35b at one of its ends. Then, being pushed by the projection 35a or 35b, the rotator 343 rotates around the horizontal shaft 342 against the urging force of the spring, which makes the lifting stage 34a or 34b tilt. The tilting of the lifting stage 34a or 34b forces any residues of the burned wax or other litters remaining thereon to slide down along the inclined plane and fall into a litter collector 36.

(4) Casting Unit F (FIGS. 1, 2, 5 and 7)

The main component of the casting unit F is a chamber composed of a cylindrical container 40 and a lid 50. The lid 50, used for closing the open top of the container 40, is separable from the container 40. The container 40 has a wheel 41, which is put around the upper part of the container 40 with a slight gap and can rotate around it. The container 40 includes a support base 42 made of an insulating material, which has a columnar cavity 43 formed at the center and a heater 44 installed on the inner circumferential wall of the cavity 43. In the space surrounded by the heater 44, a cylindrical crucible retort 45 made of a ceramic is inserted, which is designed to loosely receive the crucible B, allowing its easy removal. The upper end of the crucible retort 45 is formed like a flange extending outwards, which is pressed from above by an upper support body 46 made of a fire-resistant material. This prevents the crucible retort 45 from falling off the cavity 43 even when the chamber is reversed.

A horizontal rotation shaft 47 driven by a motor 48 is fixed to the side of the container 40. The rotation shaft 47 is formed like a tube with one end leading to the inside of the container 40. Thus, the rotation shaft 47 provides a gas passage 49 for connecting the inside of the chamber to a vacuum pump and gas inlet valve (both not shown in the figures).

The lid 50 is provided with a pushing mechanism 51 composed of a coil spring and other elements. The coil spring pushes down the ring A2 set in the chamber with the reservoir 111 directed downwards, thus tightening the contact between the top of the upper support body 46 and the bottom of the ring A2.

The lid 50 is attachable to and detachable from a lid elevator 54 vertically movable along a stand 53. In detail, the lid 50 has a pair of hooks 52 at its top, and the lid elevator 54 has a pair of holes 55 into which the hooks 52 are to be inserted. The lid elevator 54 is further provided with an engaging plate 56, which is horizontally movable back and forth by means of an air cylinder (not shown). With the hooks 52 inserted in the holes 55, when the engaging plate 56 is moved forth, the engaging plate 56 engages with the hooks 52, and the lid 50 becomes suspended on the lid elevator 54. When the engaging plate 56 is moved back, the hooks 52 are released from the engagement, and the lid 50 can be detached from the lid elevator 54.

The stand 53 has a crucible-closing lid 57, which can rotate around a horizontal shaft 58 extending in the width direction. With the crucible B1 set in the container 40 and the lid 50 separated from the container 40, the open top of the crucible B1 can be closed by pulling down the crucible-closing lid 57 onto the crucible B1. In this state, the inside of the crucible B1 is shielded from the external air, whereby the alloy ingots contained in the crucible B1 is prevented from being undesirably oxidized during the heating and melting process, which will be described later.

Figure 9:
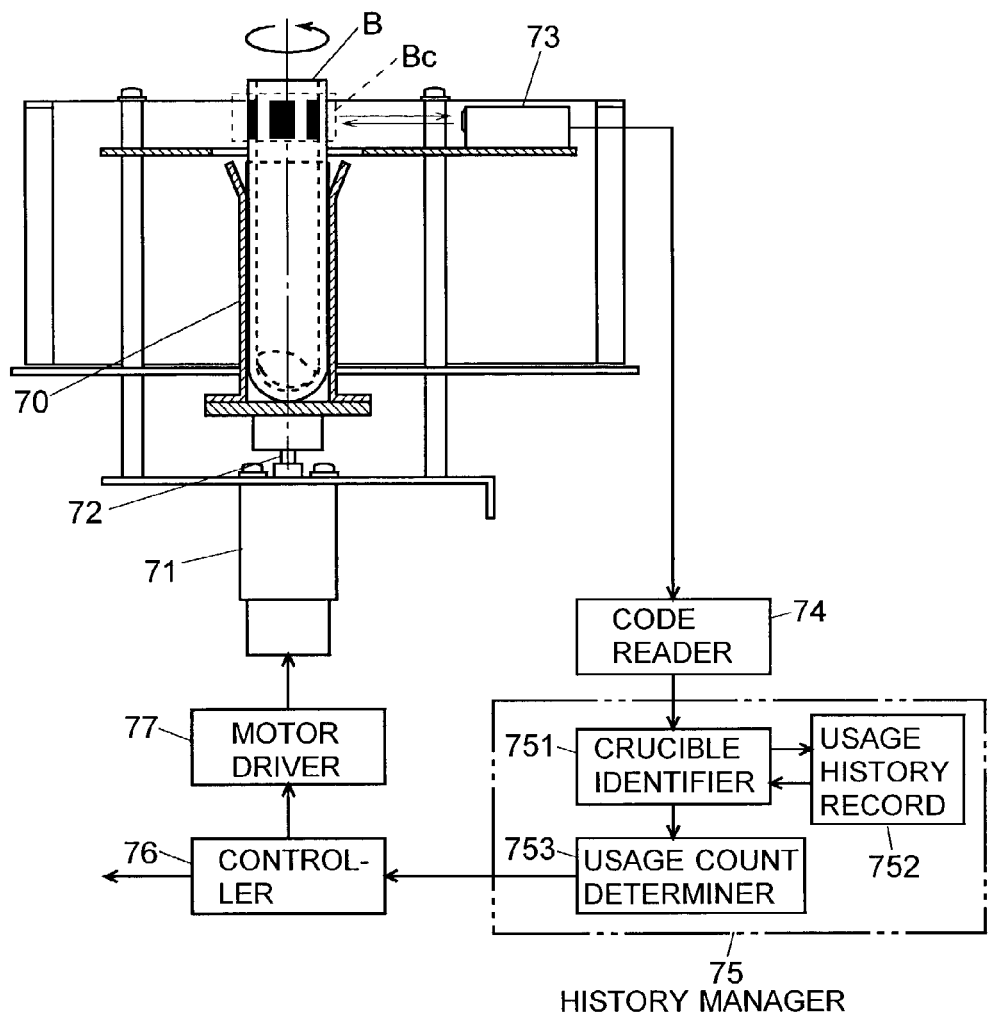
FIG. 9 is a general drawing of the crucible usage history manager G of the automatic casting apparatus of the embodiment.
Figure 10:
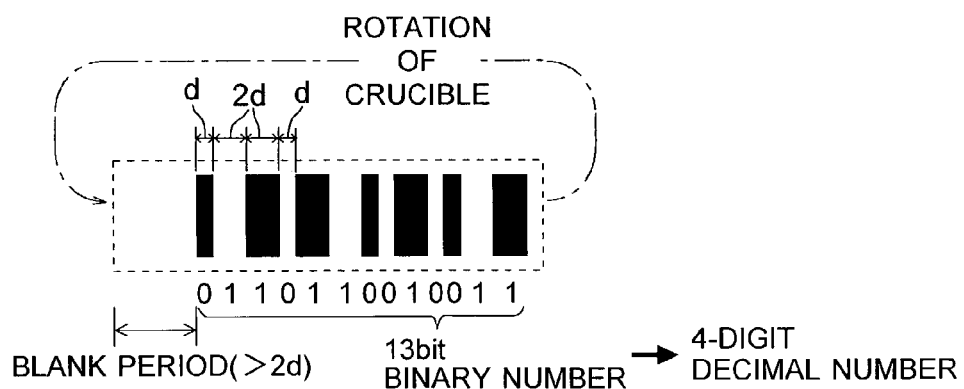
FIG. 10 shows an example of the management code printed on the crucible for the management of the usage history.

(5) Crucible Usage History Manager G (FIGS. 1, 9 and 10)

The present apparatus mainly uses two types of crucibles: ceramic crucible and carbon graphite crucible. Ceramic crucibles rapidly degrade and become easy to crack or break when used more than twenty times. An occurrence of such problems in the course of the conveying or heating operation would seriously decrease the working efficiency. Taking this into account, the present apparatus includes the crucible usage history manager G for automatically managing the usage history for each crucible, particularly that of the ceramic crucible, in order to stop using the crucible before it becomes fragile.

For the management of the usage history, each crucible is given a management number before its first usage. In this embodiment, the management number, or management code, is represented by a barcode, as shown in FIG. 10. In detail, the management code is a four-digit decimal number taking a value from 0 to 8191, which is converted into a binary number and represented by a 13-bit barcode. In FIG. 10, the bar or white space having the width d in the scanning direction represents "0", and the bar or white space having the width 2d represents "1". For example, the management code in FIG. 10 represents the management number "3475", or "0110110010011" in binary number. It is possible to arbitrarily determine the width d, taking account of the capability of the scanner. A preferable value is about 2.5 mm.

A preferable method of printing the management code on the crucible is as follows: print the management code on a thin-film adhesive seal made of a ceramic, using heat-resistant ink; put the seal onto a predetermined part of the crucible; and burn the crucible to integrate the crucible and the seal.

As shown in FIG. 9, the crucible usage history manager G includes: a holder 70 for holding a crucible in the standing position; a motor 71 for rotating the holder 70 via a shaft 72; an optical sensor 73 for scanning the management code printed on the upper part of the crucible projecting from the upper end of the holder 70; a code reader 74 for demodulating the output signal of the optical sensor 73 into the management number; a history manager 75 for checking the usage history of the crucible based on the management number; a controller 76; and a motor driver 77.

As the holder 70 holding the crucible B1 rotates, the optical sensor 73 scans the management code and produces an output signal whose level changes corresponding to the pattern of the management code. The code reader 74 checks the level of the signal with a sampling period far shorter than the minimum width d of the bar or white space of the management code, to determine the value of each digit. In each rotation of the crucible, a blank period appears in advance of the management code. The blank area has a length greater than 2d, the maximum length for the white space in the management code. Therefore, it is possible to find the head of the management code by detecting the bland period within a single rotation of the crucible.

The management number thus scanned is sent to the crucible identifier 751 of the history manager 75. The crucible identifier 751 is provided with a usage history record 752, which stores the usage counts associated with the management numbers in the form of a table, for example. On receiving the management number from the code reader 74, the crucible identifier 751 searches the usage history record 752 for the usage count of the crucible having the aforementioned management number. If the desired management number cannot be found, it means that the crucible is a new one. Therefore, the management number should be newly added to the table.

The usage count retrieved as described above is sent from the crucible identifier 751 to a usage count determiner 753, which in turn determines whether or not the usage count of the crucible is equal to or greater than a predetermined threshold value. For example, for such crucibles that suddenly become fragile after the usage count exceeds twenty, the threshold value is set at fifteen for the safety. The determination result is sent from the usage count determiner 753 to the controller 76. When the usage count of a crucible is less than the threshold value, the controller 76 continues the casting work using that crucible. When the usage count is equal to or greater than the threshold value, the controller 76 returns the above crucible to the ring/crucible-placing platform C and proceeds to the next casting work using another pair of the ring and the crucible.

When the usage count has attained the threshold value, the operator is informed of the fact by, for example, a visual display. This information enables the operator to discard the crucible. This eliminates the possibility of using a crucible that has become easy to crack or break. Thus, it is possible to assuredly prevent the crucible from breaking in the course of the conveying or casting process.

(6) Ring Reversion Detector H (FIGS. 1 and 6)

When the ring is placed upside down on the ring/crucible-placing platform C, the casting work cannot be correctly performed. Accordingly, after taking a ring A1 from the ring/crucible-placing platform C, the conveyer D conveys the ring A1 to the ring reversion detector H to check the direction of the ring before placing the ring A1 onto the lifting stage 34a or 34b of the burning unit E. The ring reversion detector H has a movable pin 90 having a predetermined height. The movable pin 90 functions as a movable element of the switch 91 located under the table 3.

After taking a ring A1 from the ring/crucible-placing platform C, the conveyer D conveys the ring A1 to a position above the movable pin 90 of the ring reversion detector H and lowers the ring A1 to a predetermined level, as shown in FIGS. 6A and 6B. When the direction of the ring A1 is correct, the reservoir of the ring A1 is located at the bottom, as shown in FIG. 6A, so that the investment material in the ring does not contact the movable pin 90. When, on the other hand, the ring A1 is upside down, the bottom side of the ring A1 is filled with the investment material, as shown FIG. 6B, so that the movable pin 90 is pushed down, activating the switch 91. Thus, it is possible to detect the reversion of the ring A1 from the activation/deactivation of the switch 91.

Figure 8:
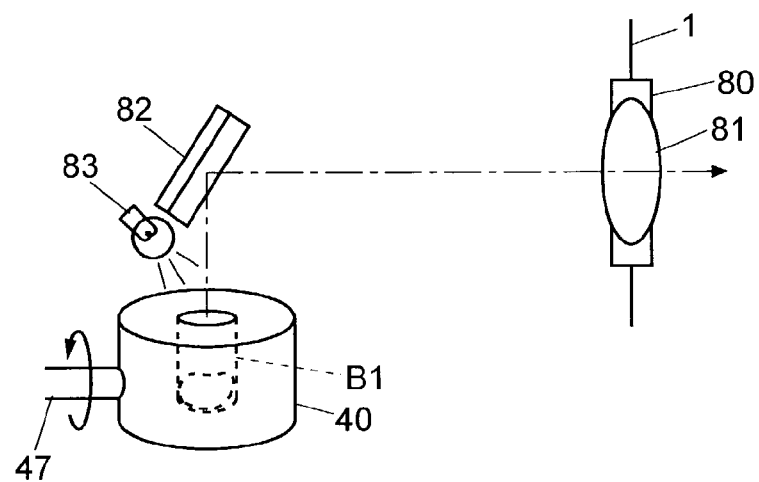
FIG. 8 is an outlined drawing of the crucible inspection mechanism J of the automatic casting apparatus of the embodiment.

(7) Crucible Inspection Mechanism J (FIGS. 1 and 8)

Various kinds of metals are used as the casting material, ranging from low-melting metals to high-melting metals. In the case of using a material that has not been used before, the heating temperature, heating time or other conditions may be unknown. Then, it is desirable to visually check whether or not the metal has been completely melted in the crucible. The crucible inspection mechanism J helps with such a case. The crucible inspection mechanism J includes a mirror 82 located in the upper right part of the chamber, a lens 81 located in the front side of the cover 1 at a position almost in front of the mirror 81, and a window 80 with the lens 81 fitted in. In addition, a lamp 83 for illuminating the inside of the crucible B contained in the container 40 of the chamber is provided near the mirror 82.

While being heated in the container 40, the crucible B1 is in the standing position. Then, when the operator presses a button of the operation unit for starting the inspection of the crucible, the controller controls the crucible-closing lid 57 to be lifted from the top of the crucible B1 to disclose the top of the crucible B1. Then, the motor 48 is energized to rotate the container 40, and then stopped at a position where the crucible B1 is inclined by a predetermined angle. In this position, the mirror 82 projects an image of the inside of the crucible B1 to the lens 81, which in turn provides an enlarged image to the operator looking into the window 80. When the metal has a high-melting point, the molten state of the metal in the crucible B1 can be easily checked from whether or not the metal is glowing. In the case of using a low-melting metal that does not glow when heated, it is still possible to check the molten state of the metal by illuminating the metal with the lamp 83 and checking whether or not the surface of the metal is like a mirror.

Thus, the operator can check the molten state of the casting material in the crucible B1 from the outside of the cover 1 whenever necessary as long as it is in advance of the pouring process.

Figure 11:
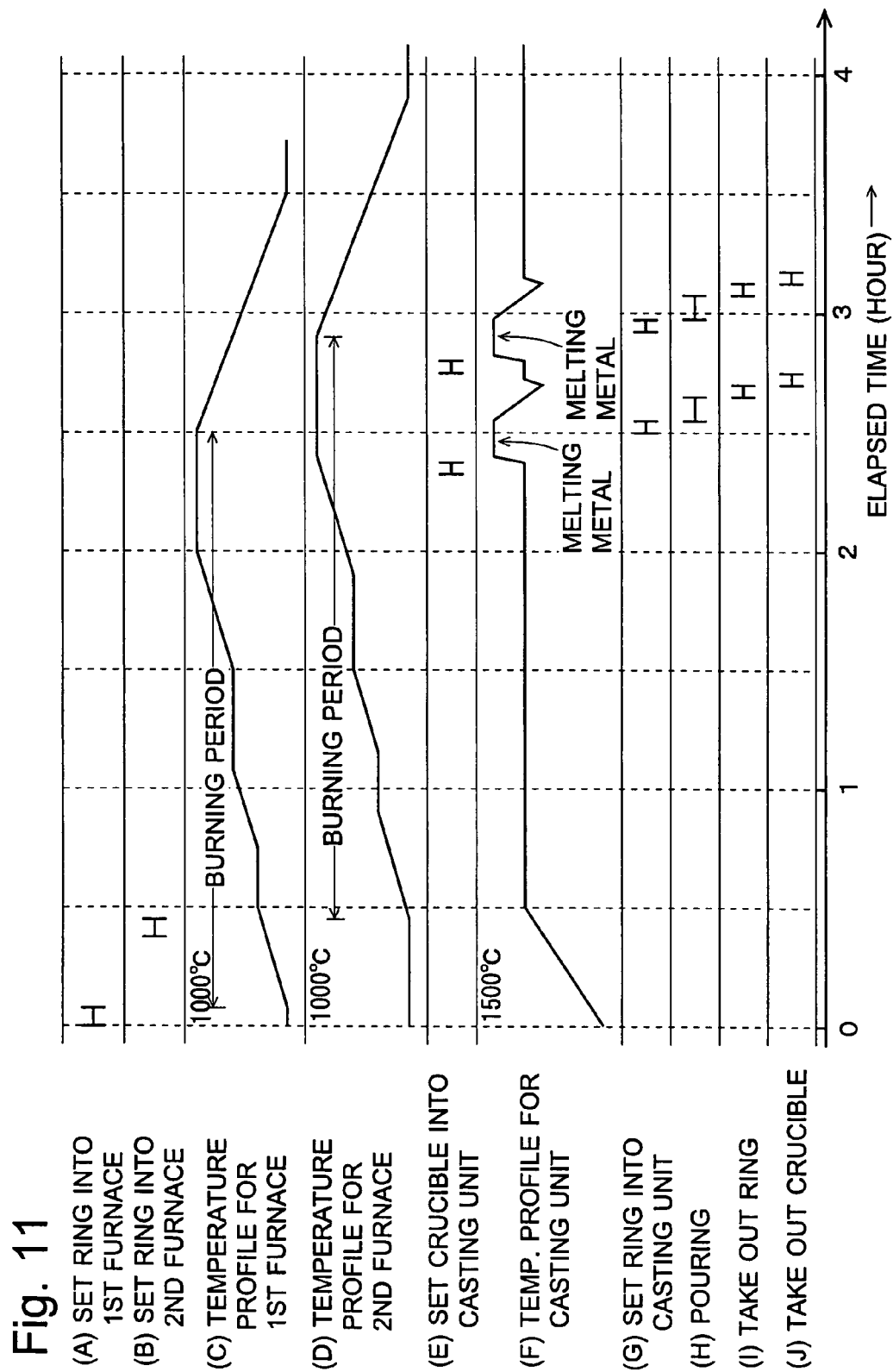
FIG. 11 is a sequence chart showing the general operation of the casting apparatus of the embodiment.

The general operation of the apparatus for casting dental prosthesis of the present embodiment is described below in the working order, with reference to FIG. 11 showing an example of the control sequence of the operation. The following description assumes that two pieces of dental prostheses are to be manufactured.

Figure 12:
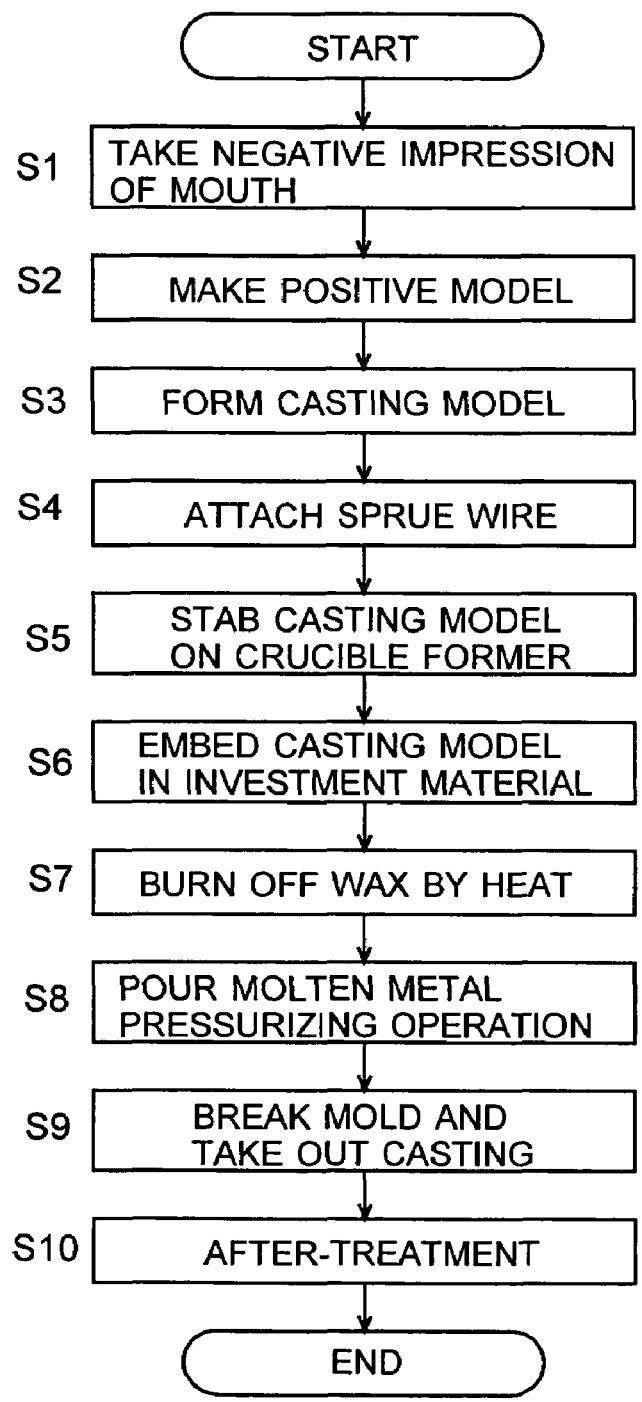
FIG. 12 is a flowchart showing the steps of casting a dental prosthesis by the lost wax method.
Figure 13:
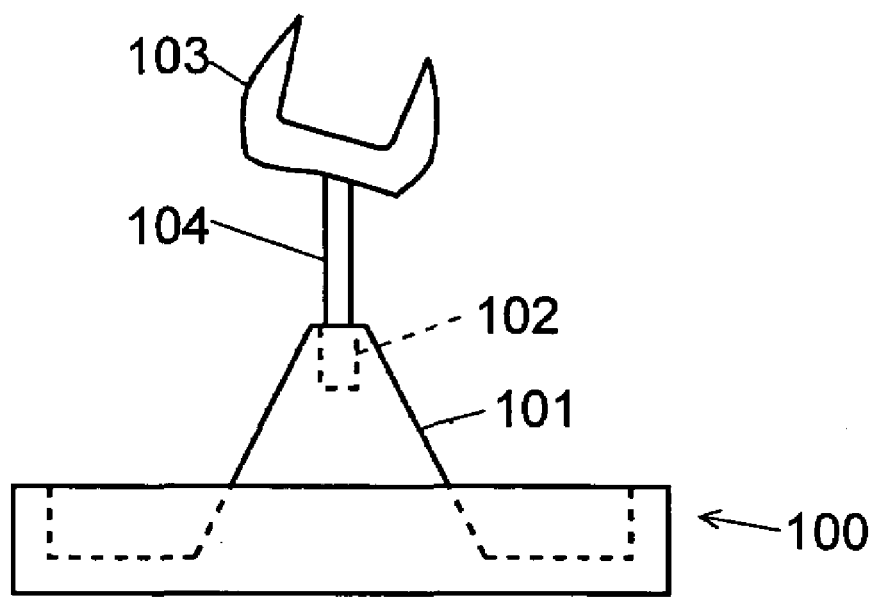
FIG. 13 shows a casting model mounted on a commonly used crucible former.

The operator sets two pairs of the ring A1 and the crucible B1 onto or into the ring/crucible-placing platform C. Each ring A1 should be placed above the crucible B1 containing the casting material (metal ingots) corresponding to the ring A1. The ring A1 to be placed onto the ring/crucible-placing platform C is manufactured by the steps S1–S6 shown in FIG. 12, for example.

In advance of giving a command for starting the operation, the operator sets the casting conditions through the operation panel. The apparatus has build-in data of the temperature profiles and other casting conditions for typical investment materials and casting materials used for manufacturing dental prostheses. Accordingly, the operator needs only to select the name of the material to appropriately set the casing conditions. Furthermore, the apparatus allows the operator to make a detailed setting of the casting conditions and store the setting in the storage device (not shown) so that it can be used in future casting work.

Next, the operator operates the switch for starting the operation. In response to this switch operation, the control circuit controls the conveyer D to correct the position of the first ring A1.

That is, the motor 29 is energized to drive the chain belt 29 to move the carriage 21 of the conveyer D from the initial position (the right-most position in FIG. 1 or 2, for example) to a predetermined position. At this moment, the fingers 226 of the gripper 22 are fully opened. Then, the arm 215 is rotated so that the fingers 226 come to the position above the ring A1, and is lowered to a predetermined level where the lower ends of the fingers 226 are at a small distance from the top of the ring/crucible-placing platform C. After that, the air cylinder 221 is driven to simultaneously move the four fingers 226 inwards. In this motion, the fingers 226 push the ring A1 into the correct position if the ring A1 is displaced from the correct position. When no ring A1 is present on the ring-placing area 10 concerned, the fingers 226 eventually reach the inner-most position. Taking this into account, it is possible to construct a mechanism for generating a signal when the fingers 226 reach the inner-most position, meaning that no ring is placed on the ring-placing area 10.

After the above-described operation, the fingers 226 are opened, then raised to a predetermined level, and again moved inwards to hold the ring A1 at its upper part. Then, the leg 212 is expanded to raise the arm 215. Subsequently, the arm 215 is rotated around the main shaft 214 by about 180 degrees so that the ring A1 comes to the position above the movable pin 90 of the ring reversion detector H. Then, the ring A1 is lowered to the aforementioned level to check whether the direction of the ring A1 is correct. If the direction is correct, the operation is allowed to proceed, and the conveyer D conveys the ring A1 onto the lifting stage 34a of the burning unit E standing by at the intermediate position. After that, the arm 215 is rotated away from the lifting stage 34a. When, on the other hand, the ring A1 is upside down, it pushes the movable pin 90 of the ring reversion detector H, which in turn generates a detection signal. On receiving this signal, the control circuit controls the conveyer D to return the ring A1 to the ring/crucible-placing platform C, and starts the conveying operation for the next ring A1.

Starting from the state where the ring A1 is placed on the lifting stage 34a as shown in FIG. 4 with solid lines, the lifting stage 34a is elevated until it closes the lower opening of the furnace 32a with the ring A1 contained inside. Then, the heater (not shown) of the furnace 32a is energized so that the temperature is raised according to a predetermined temperature profile. In this embodiment, the temperature is raised step by step to 700–900° C. in about two hours, as shown by the chart (C) in FIG. 11.

After the first ring A1 is set in the furnace 32a as described above, the conveyer D stands by for a while and, after a preset period of time, restarts its operation to convey the second ring A1 into the second furnace 32b, operating similar to the above-described case. This embodiment assumes that the two rings should be heated under the same conditions. Accordingly, the second furnace 32b also heats the ring A1 according to the same temperature profile as used by the first furnace 32a. When, for example, the two rings contain different investment materials, the temperature profile should be appropriately determined for each ring.

Figure 7:
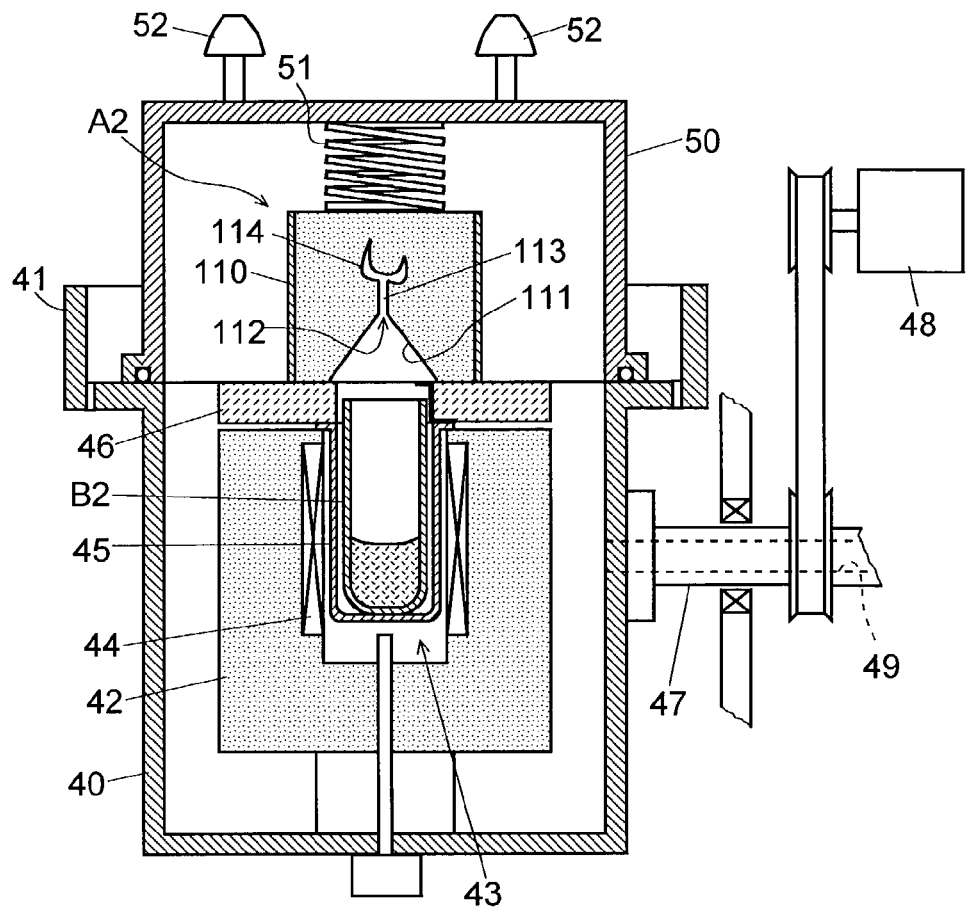
FIG. 7 is a vertical sectional view of the chamber of the automatic casting apparatus of the embodiment.

In the burning process, the wax embedded in the investment material in the ring A1 is burned off, leaving a cavity corresponding the casting model. Thus, the mold is obtained. As shown in FIG. 7, the ring A2 has a cylindrical ring 110 made of a metal covering the circumferential side. Inside the ring A2, a sprue runner 113 leading to a sprue gate 112 formed at the apex of the reservoir 111, and the cavity 114 corresponding to the casting model, are formed.

Before the ring A1 is burned in the furnace 32a as described above, the conveyer D conveys the crucible B1 corresponding to the ring A1 from the ring/crucible-placing platform C to the crucible usage history manager G. After the usage count of the crucible B1 is checked with the crucible usage history manager G as described above, the crucible B1 is returned to the ring/crucible-placing platform C. When the usage count is less than the threshold value, the burning of the ring is started and, after a preset period of time, the conveyer D conveys the crucible B1 into the crucible retort 45 in the container 40 of the chamber. When, on the other hand, the usage count is equal to or greater than the threshold value, it is not allowed to use the crucible B1. Accordingly, the conveyer D returns the ring A1 from the lifting stage 34a of the burning unit E to the ring/crucible-placing platform C, and the casting operation using that pair of the ring A1 and the crucible B1 is left undone, as in the case of the upside-down placement of the ring.

As shown by the chart (F) in FIG. 11, the heater 44 in the chamber is supplied with a heating current from the start of the operation, and is maintained at a predetermined temperature when the crucible B1 is conveyed into the container 40. After the crucible B1 is set in the container 40, the crucible-closing lid 57 falls forward from the stand-by position, closes the open top of the crucible B1 and supplies argon gas. This prevents the oxidation of the casting material. Then, the heating current is increased so that the crucible is heated to a temperature where the metal assuredly melts (approximately 1000° C. for precious metal, or 1400° C. for non-precious metal). This temperature is maintained for a preset period of time, during which the ingots in the crucible melt into liquid.

When the preset period of time has lapsed, the metal ingots are melted enough to be poured into the mold. Then, the crucible-closing lid 57 is lifted up, and the ring A2 is conveyed from the burning unit E to the casting unit F as follows. The lifting stage 34a of the burning unit E is lowered to the intermediate position with the ring A2 placed thereon. Then, the conveyer D holds the ring A2 with the fingers 226, slides along the guide rails, and places the ring A2 onto the crucible B2 in the container 40. Then, the arm 215 moves away from the container 40, and the lid elevator 54 descends with the lid 50. The lid elevator 54 stops when the lid 50 reaches the top of the container 40.

After that, the gas inlet valve (not shown) is closed, and the vacuum pump is energized, whereby the air in the chamber is removed through the gas passage 49 to the outside. The pressure in the chamber is monitored with a pressure sensor (not shown). When the pressure has reached a preset value (−0.1 Mpa, for example), the engaging plate 56 is moved back to resolve the engagement with the hooks 52. After that, the lid elevator 54 moves upward, while the lid 50 is left closing the open top of the container 40. Subsequently, the control circuit gives a command for driving the motor 58 to rotate the chamber clockwise from the normal position by about 180 degrees. The rotation of the chamber brings the lid 50 into the locked state.

When the molten metal in the crucible B1 has an adequate fluidity, a certain amount of inclination of the chamber makes the molten metal flow from the inclined crucible B1 into the reservoir 111 of the ring A1. When the chamber has reached the reversed position, or at a proper time point earlier than that, the vacuum pump is stopped, and the gas inlet valve is opened to start the pressurizing process. Then, a compressed air or inert gas rapidly flows through the gas passage 49 into the chamber, and the air or gas further flows through the gap between the open top of the crucible B2 and the ring A2 into the reservoir 111. In this process, the sprue gate 112 is completely closed by the molten metal supplied from the crucible B2 into the reservoir 111, and then the air or gas flows into the reservoir 111 to press the top of the molten metal. Since the chamber is maintained in the vacuum state until immediately before the introduction of the air or gas, the sprue runner 113 and the cavity 114, being closed by the molten metal, is still in the vacuum state. Therefore, the molten metal existing at the sprue gate 112 is forced to flow through the sprue runner 113 into the cavity 114 by the differential pressure between the reservoir 111 and the cavity 114.

When the chamber has reached the reversed position, the control circuit gives a command for stopping the motor 48, and for terminating the power supply to the heater 44 after a preset period of time. After the termination of the power supply to the heater 44, the inside of the chamber is naturally cooled, and the molten metal filling the cavity 114 of the ring A2 starts solidifying. After continuing the pressurizing process for a preset period of time to make the molten metal almost solid, the gas inlet valve is closed, and the vacuum pump is energized again. This makes the lid 50 pulled onto the container 40 by the differential pressure. Then, the control circuit gives a command for driving the motor 48 to rotate the chamber counterclockwise from the reversed position to the normal position.

When the chamber has reached the normal position, the motor 48 is stopped. Subsequently, the lid elevator 54 descends to the level where the hooks 52 of the lid 50 are inserted into the holes 55. Then, the vacuum pump is stopped, so that the air gradually flows into the chamber, breaking the vacuum state inside. This decreases the difference in pressure between the inside and the outside. After the pressure difference has been adequately small, the lid elevator 54, with the engaging plate 56 engaged with the hooks 52, moves upward with the lid 50. Thus, the chamber is opened. After that, the conveyer D grips the processed ring, and throws it into the ring collection port 6 below the burning unit E. Also, the conveyer D takes out the crucible from the container 40, and returns it to the ring/crucible-placing platform C.

Next, the casting operation for the second ring, standing by in the furnace 32*b,* is carried out. That is, the conveyer D takes the second crucible B1, which has passed the usage history checking, from the ring/crucible-placing platform C, and conveys it into the container 40. After the metal ingots in the crucible have been adequately melted in the container 40, the conveyer D conveys the ring A2 from the furnace 32*b* onto the crucible B2. Subsequently, the casting process for the second ring is carried out in the same manner as in the case of the first ring, as described above.

The apparatus of this embodiment is capable of carrying out the casting operation for three to six pieces of rings basically in the same manner as described above. As is clear from FIG. 11, it is the burning of the ring that requires the longest time in the entire process. Accordingly, it is preferable to program the control sequence so that each of the two furnaces 32*a* and 32*b* is supplied with the rings without a break. This provides the highest efficiency (or the shortest time) of processing the six rings.

After the ring in the collection chamber 4 has adequately cooled down, the operator pulls the mold out of the metallic ring 110, and breaks the mold to take out the cast, i.e. the dental prosthesis.

It should be noted that the above embodiment is a mere example of the present invention, which can be modified or changed within the scope of the invention.

What is claimed is:

1. An apparatus for casting dental prosthesis comprising:
    a) a ring-placing section, formed like a platform, onto which plural rings are to be placed, each ring having a casting model of a heat-subliming material embedded inside;
    b) a crucible holder for holding plural cylindrical crucibles in a standing position, each crucible containing a casting material corresponding to each of the plural rings;
    c) a burning unit having a vertically movable lifting stage onto which each of the rings are to be placed, and a furnace which covers each of the rings placed on the lifting stage when the lifting stage is elevated, and heats each of the rings to form a mold;
    d) a casting unit having a chamber composed of a container for containing and heating the crucible, and a lid for covering an open top of the container while holding the mold in such a position where a sprue gate of the mold is located above the open top of the crucible contained in the container, and a chamber driver for melting the casting material in the crucible and then rotating the chamber from a normal position to a reversed position to pour the casting material into the mold; and
    e) a conveyer for conveying each of the rings or the crucible between the ring-placing section, the crucible holder, the burning unit and the casting unit, where the conveyer includes a gripper for holding each of the rings and the crucible, a vertical actuator for vertically moving the gripper, and a horizontal actuator for horizontally moving the gripper.

2. The apparatus for casting dental prosthesis according to claim 1, wherein:
    the conveyer performs a position-correcting motion for correcting the position of each of the rings by lowering the gripper to a level close to a bottom of each of the rings and making a gripping motion with the gripper in advance of conveying each of the rings from the ring-placing section.

3. The apparatus for casting dental prosthesis according to claim 1, further comprising:
    a) a crucible rotator for holding the crucible in a standing position and rotating the crucible at a preset speed around a vertical axis passing through the center of the crucible;
    b) a code reader for reading the management code on the crucible while the crucible is rotated by the rotator;
    c) a usage history manager for managing a usage history of each crucible based on the management code read by the code reader; and
    d) a controller for checking whether a cumulative usage count of the crucible has attained a predetermined count, and for determining, based on the result of the checking, whether a casting operation using the crucible is acceptable.

4. The apparatus for casting dental prosthesis according to claim 1, wherein:
    the lifting stage of the burning unit includes:
    a base capable of rotating around a substantially horizontal axis, an orientation-maintaining mechanism for maintaining the base substantially horizontal when no external force is exerted on the base, and an orientation-changing mechanism for exerting an external force onto the base to change the orientation of the base when the base is lowered to a predetermined level.

5. The apparatus for casting dental prosthesis according to claim 1, further comprising:
    a ring reversion detector having a movable element to be pressed by the opposite side of the ring on which the reservoir is not present when the ring gripped by the conveyer is lowered to a preset level, and a detector for detecting the motion of the movable element; and
    wherein the ring has a reservoir on one side.

6. The apparatus for casting dental prosthesis according to claim 1, further comprising:
    a casing for containing the casting unit and the conveying unit;
    an inclination determiner for maintaining a rotational position of the chamber so that the crucible is inclined by a preset angle before the mold is conveyed to the position above the crucible contained in the container; and
    a crucible inspection mechanism having at least one mirror located so that an inside of the crucible inclined can be observed through it, a lens for enlarging an image reflected in the mirror, a lighting device for illuminating the inside of the crucible inclined, and an opening formed in the outside of the casing for allowing a view of the enlarged image created by the lens.

\* \* \* \* \*